(12) United States Patent
Roth et al.

(10) Patent No.: US 11,267,854 B2
(45) Date of Patent: Mar. 8, 2022

(54) COMPLEX-SPECIFIC STANDARDIZATION OF IMMUNOLOGICAL METHODS FOR THE QUANTIFICATION OF S100A12

(71) Applicant: Westfaelische Wilhelms-Universitaet Muenster, Muenster (DE)

(72) Inventors: Johannes Roth, Muenster (DE); Thomas Vogl, Muenster (DE)

(73) Assignee: Westfaelische Wilhelms-Universitaet Muenster, Muenster (DE)

(*) Notice: Subject to any disclaimer, the term of this patent is extended or adjusted under 35 U.S.C. 154(b) by 92 days.

(21) Appl. No.: 16/318,854

(22) PCT Filed: Jul. 18, 2017

(86) PCT No.: PCT/EP2017/068100
§ 371 (c)(1),
(2) Date: Jan. 18, 2019

(87) PCT Pub. No.: WO2018/015375
PCT Pub. Date: Jan. 25, 2018

(65) Prior Publication Data
US 2019/0185530 A1 Jun. 20, 2019

(30) Foreign Application Priority Data
Jul. 20, 2016 (EP) ..................... 16180284

(51) Int. Cl.
*C07K 14/47* (2006.01)
*G01N 33/566* (2006.01)

(52) U.S. Cl.
CPC .......... *C07K 14/4728* (2013.01); *C07K 14/47* (2013.01); *G01N 33/566* (2013.01); *G01N 2333/4727* (2013.01); *G01N 2800/065* (2013.01); *G01N 2800/105* (2013.01); *G01N 2800/125* (2013.01); *G01N 2800/205* (2013.01); *G01N 2800/24* (2013.01); *G01N 2800/32* (2013.01); *G01N 2800/56* (2013.01)

(58) Field of Classification Search
CPC ............. C07K 14/4728; G01N 33/566; G01N 2800/065; G01N 2800/105; G01N 2800/125; G01N 2333/4727
See application file for complete search history.

(56) References Cited

U.S. PATENT DOCUMENTS

| | | | |
|---|---|---|---|
| 5,455,160 | A | 10/1995 | Fagerhol et al. |
| 6,020,135 | A | 2/2000 | Levine et al. |
| 6,028,060 | A | 2/2000 | Hellerqvist et al. |
| 6,313,267 | B1 | 11/2001 | Hitomi et al. |
| 6,555,340 | B1 | 4/2003 | Schmidt et al. |
| 7,011,952 | B2 | 3/2006 | Hageman et al. |
| 2002/0037538 | A1 | 3/2002 | Trepicchio et al. |
| 2002/0072484 | A1 | 6/2002 | Alters et al. |
| 2003/0055215 | A1 | 3/2003 | Hitomi et al. |
| 2003/0154032 | A1 | 8/2003 | Pittman et al. |
| 2003/0175713 | A1 | 9/2003 | Sorg et al. |
| 2005/0147972 | A1 | 7/2005 | Roth et al. |
| 2009/0111161 | A1* | 4/2009 | Jones ................. C12N 9/52 435/220 |
| 2010/0311758 | A1 | 12/2010 | Roth et al. |

FOREIGN PATENT DOCUMENTS

| | | |
|---|---|---|
| EP | 0731166 A2 | 11/1996 |
| WO | 0020621 | 4/2000 |
| WO | 0186002 A2 | 11/2001 |
| WO | 0248310 A2 | 6/2002 |
| WO | 03060465 A2 | 7/2003 |
| WO | 03069341 A2 | 8/2003 |
| WO | 2003069341 A2 | 8/2003 |
| WO | 2011146479 A1 | 11/2011 |
| WO | 2012175602 A2 | 12/2012 |
| WO | 2013132347 A2 | 9/2013 |
| WO | 2014037588 A2 | 3/2014 |

OTHER PUBLICATIONS

Campbell (from Monoclonal Antibody Technology, Elsevier Sci Pub. 1984, total 16 pages) (Year: 1984).*
Hatakeyama et al. (Eur. J. Biochem. 2007 vol. 271, p. 3765-3775) (Year: 2004).*
Brophy et al. (JACS 2013 135: 17804-17817) (Year: 2013).*
Cunden, L.S., et al. (2016) "Calcium ions tune the zinc-sequestering properties and antimicrobial activity of human S100A12", Chemical Science, 7:1338-1348.
Cunden, L.S., et al. (2015) "Supplementary Information for Calcium Ions Tune the Zinc-Sequestering Properties and Antimicrobial Activities of Human S100A12", The Royal Society of Chemistry, 24 pages.
Moroz, O.V., et al., (2003) "Multiple Stuctural States of S1 00A 12: A Key to Its Functional Diversity", Microscopy Research and Technique, 60:581-592.
Garcia, A.F., et al., (2008) "Structural stability and reversible unfolding of recombinant porcine S100A12", Biophysical Chemistry, 134:246-253.
Goyette, J., et al., (2009) "Pleiotropic Roles of S100A12 in Coronary Atherosclerotic Plaque Formation and Rupture", The Journal of Immunology, 183:593-603.
Leukert, N., et al., (2006) "Calcium-dependent Tetramer Formation of S100A8 and S100A9 is Essential for Biological Activity", J. Mol. Biol., 359:961-972.

(Continued)

Primary Examiner — Changhwa J Cheu
(74) Attorney, Agent, or Firm — Kagan Binder, PLLC

(57) ABSTRACT

The present invention relates to mutants of S100A12 having at least one mutation in the high-affinity calcium binding hand or the low-affinity calcium binding hand or the zinc binding region. The present invention also relates to methods of detecting S100A12 dimers in a sample as well as methods of diagnosis using the S100A12 mutant of the invention, as well as to diagnostic compositions and kits comprising such an S100A12 mutant. The present invention further relates to a method of generating an antibody that specifically binds to an S100A12 dimer using the S100A12 mutant of the invention, as well as to an antibody that specifically binds to an S100A12 dimer.

13 Claims, 6 Drawing Sheets

Specification includes a Sequence Listing.

(56) References Cited

OTHER PUBLICATIONS

Champaiboon et al. (2009) "Calprotectin S100A9 Calcium-binding Loops I and II Are Essential for Keratinocyte Resistance to Bacterial Invasion", The Journal of Biological Chemistry, 284:7078-7090.
Luegering et al. (1995) "Immunohistochemical Distributional and Serum Levels of the Ca2+-Binding Proteins MRP8, MRP14 and Their Heterodimeric Form MRP8/14 in Crohn's Disease", Digestion, 56:406-414.
Striz et al. (2004) "Calprotectin—a Pleiotropic Molecule in Acute and Chronic Inflammation" Physiol. Res., 53:245-253.
Vogl et al. (2012) "Pro-Inflammatory S100A8 and S100A9 Proteins: Self-Assembly into Multifunctional Native and Amyloid Complexes", Int. J. Mol. Sci., 13:2893-2917.
Roth et al. (1993) "MRPS and MRP14, S-100-Like Proteins Associated With Myeloid Differentiation, Are Translocated to Plasma Membrane and Intermediate Filaments in a Calcium-Dependent Manner", Blood, 82:1875-1883.
Corada et al. (2001) "Monoclonal antibodies directed to different regions of vascular endothelial cadherin extracellular domain affect adhesion and clustering of the protein and modulate endothelial permeability", Blood, 97:1679-1684.
Padlan et al (1996) "X-Ray Crystallography of Antibodies", Advances in Protein Chemistry, 49:57-133.
Chabaud et al. (2001) "The Combination of Tumor Necrosis Factor a Blockade With Interleukin-1 and Interleukin-17 Blockade is More Effective for Controlling Synovial Inflammation and Bone Resorption in an Ex Vivo Model", Arthritis & Rheumatism, 44: 1293-1303.
Lorenz et al. (2001) "New therapeutic options for the treatment of Rheumatoid Arthritis", Z. Rheumatol., 60:326-332, (English Summary).
Shouda et al. (2001) "Induction of the cytokine signal regulator SOCS3/CIS3 as a therapeutic strategy for treating inflammatory arthritis", J. Clin. Invest., 108:1781-1788.
Ly et al. (2014) "A proteomic chronology of gene expression through the cell cycle in human myeloid leukemia cells", eLife, 3, e01630:1-38.
Yang et al. (2001) "Proinflammatory properties of the human S100 protein S100A12", Journal of Leukocyte Biology, 69:986-994.
Sunahori et al. (2006) "The S100A8/A9 heterodimer amplifies proinflammatory cytokine production by macrophages via activation of nuclear factor kappa B p38 mitogen-activated protein kinase in rheumatoid arthritis", Arthritis Research and Therapy, 8, R69:1-12.
Alamanos et al. (2005) "Epidemiology of adult rheumatoid arthritis", Autoimmunity Reviews, 4:103-136.
Bresnihan et al. (1999) "Synovial tissue analysis in rheumatoid arthritis" Bailliers's Clinical Rheumatology, 13:645-659.
Christophers (2001) "Psoriasis—epidemiology and clinical sprectrum" Clinical and Experimental Dermatology, 26:314-320.
Donato et al. (2013) "Functions of S100 Proteins", Curr. Mol. Med., 13:24-57.
Edwards et al. (2005) "Early Environmental Factos and Rheumatoid Arthritis", Clinical and Experimentsl Immunology, 143:1-5.
Giannini et al. (1993) "Methotrexate in Juvenile Rheumatoid Arthritis", Drug Safety, 9:325-339.
Giannini et al. (1987) "Poor correlation between the erythrocyte sedimentation rate and clinical activity in juvenile rheumatoid arthritis", Clinical Rheumatology, 6:197-201.
Hinks et al. (2013) "Dense genotyping of immune-related disease regions identifies 14 new susceptibility loci for juvenile idiopathic arthritis", Nature Genetics, 45:664-669.
Liao et al. (2004) "Use of Mass Spectrometry to Identify Protein Biomarkers of Disease Severity• in the Synovial Fluid and Serum of Patients With Rheumatoid Arthritis" Arthritis and Rheumatism, 50:3792-3803.
Marenholz et al. (2004) "S100 proteins in mouse and man: from evolution to function and pathology (including an update of the nomenclature)", Biochemical and Biophysical Research Communications, 322:111-1122.
Okada et al. (2014) "Genetics of rheumatoid arthritis contributes to biology and drug discovery", Nature, 506:376-381, Plus Appendix.
Ravelli et al. (1995) "Frequency of Relapse after Discontinuation of Methotrexate Therapy for Clinical Remission in Juvenile Rheumatoid Arthritis", The Journal of Rheumatology, 22:1574-1576.
Sakigawa et al. (2008) "Protein biomarker analysis by mass spectrometry in patients with rheumatoid arthritis receiving anti-tumor necrosis factor—a antibody therapy", Clinical and Experimental Rheumatology. 26:261-267.
Dai et al. (2010) "Elevated serum glucose-6-phosphate isomerase correlates with histological disease activity and clinical improvement after initiation of therapy in patients with rheumatoid arthritis", J. Rheumatol., 37:2452-61.
Zhang et al. (2013) "Value of four serum markers in the diagnosis of rheumatoid arthritis", Nan Fang Yi Ke Da Xue Bao 33:538-541; Abstract only.
Chen et al. (2010) "Diagnostic value of glucose-6-phosphate isomerase in rheumatoid arthritis patients: systematic review", Shen Wu Yi Xue Gong Cheng Eue Za Zhi 27:157-64; Abstract only.
Schaller et al. (2006) "Patients with inflammatory arthritic diseases harbo_r elevated serum and synovial fluid levels of free and immune-complexed glucose-6-phosphate isomerase (G6PI)", Biochemical. Biophys. Res. Commun., 349:838-845; Abstract only.
Hofmann et al. (2002) "RAGE and arthritis: the G82S polymorphism amplifies the inflammatory response", Genes and Immunity, 3:123-135.
Frosch et al. (2000) "Myeloid-Related Proteins 8 and 14 Are Specifically Secreted During Interaction of Phagocytes and Activated Endothelium and Are Useful Markers for Monitoring Disease Activity in Pauciarticular-Onset Juvenile Rheumatoid Arthritis", Arthritis & Rheumatism, 43:628-637.

* cited by examiner

Figure 1

```
CLUSTAL O(1.2.1) multiple sequence alignment humS100A12      -----mtkleehlegivnifhqysvrkghfdtlskgelkqlltkelantikn-ikdkavi  54
humS100A9       -mtckmsqlernietiintfhqysvklghpdtlnqgefkelvrkdlqnflkkenknekvi  59

S100A12         deifqgldanqdeqvdfqefislvaialkaahyhthke-----------------      92
humS100A9       ehimedldtnadkqlsfeefimlmarltwashekmhegde-gpghhhkpglgegtp     114
```

Figure 2

```
Human           --MTKLEEHLEGIVNIFHQYSVRKGHFDTLSKGELKQLLTKELANTIKNIKDKAVIDEIF
Canine          --MTKLEDHLEGIVDVFHRYSARVGHPDTLSKGEMKQLIIRELPNTLKNTKDQATVDKLF
Equine          EKMTKLEDHLEGVINIFHQYSARVGHFDTLSKGELKQLITRELANSIKNTKDKATIDQIF
Bovine          --MTKLEDHLEGIINIFHQYSVRVGHFDTLNKRELKQLITKELPKTLQNTKDQPTIDKIF Human           QGLDANQDEQVDFQEFISLVAIALKAAHYHTHKE     (SEQ ID NO: 01)
Canine          QDLDADKDGQVNFNEFISLVSVVLDTSHKNTHKE     (SEQ ID NO: 02)
Equine          QDLDADKDGQVSFNEFVVLVCKVLKTAHEDIHKE     (SEQ ID NO: 03)
Bovine          QDLDADKDGAVSFEEFVVLVSRVLKTAHIDIHKE     (SEQ ID NO: 04)
```

```
           10         20         30         40         50
MTKLEEHLEG IVNIFHQYSV RKGHFDTLSK GELKQLLTKE LANTIKNIKD
           60         70         80         90
KAVIDEIFQG LDANQDEQVD FQAFISLVAI ALKAAHYHTH KE
```

(SEQ ID NO: 05)

Figure 3B

```
           10         20         30         40         50
MTKLEEHLEG IVNIFHQYSV RKGHFDTLSK GELKQLLTKE LANTIKNIKD
           60         70         80         90
KAVIDEIFQG LDAAQDEQVD FQEFISLVAI ALKAAHYHTH KE
```

(SEQ ID NO: 06)

Figure 3C

```
           10         20         30         40         50
MTKLEEHLEG IVNIFHQYSV RKGHFDTLSK GELKQLLTKE LANTIKNIKD
           60         70         80         90
KAVIDEIFQG LDAAQDEQVD FQAFISLVAI ALKAAHYHTH KE
```

(SEQ ID NO: 07)

| Recombinant proteins | Experimental mass (Da) | Theoretical mass (SwissProt) (Da) |
|---|---|---|
| S100A8 | 10835.6±0.5 | 10835.0 |
| S100A9 | 13112.0±0.5 | 13111.0 |
| S100A9(N69A) | 13068.2±0.4 | 13068.0 |
| S100A9(E78A) | 13053.0±0.6 | 13053.0 |
| S100A9(N69A+E78A) | 13009.8±0.4 | 13009.7 |

SEQUENCE LISTING

<160> NUMBER OF SEQ ID NOS: 9

<210> SEQ ID NO 1
<211> LENGTH: 92
<212> TYPE: PRT
<213> ORGANISM: Human

<400> SEQUENCE: 1

Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Asn
    50                  55                  60

Gln Asp Glu Gln Val Asp Phe Gln Glu Phe Ile Ser Leu Val Ala Ile
65                  70                  75                  80

Ala Leu Lys Ala Ala His Tyr His Thr His Lys Glu
                85                  90

<210> SEQ ID NO 2
<211> LENGTH: 92
<212> TYPE: PRT
<213> ORGANISM: Dog

<400> SEQUENCE: 2

Met Thr Lys Leu Glu Asp His Leu Glu Gly Ile Val Asp Val Phe His
1               5                   10                  15

Arg Tyr Ser Ala Arg Val Gly His Pro Asp Thr Leu Ser Lys Gly Glu
            20                  25                  30

Met Lys Gln Leu Ile Ile Arg Glu Leu Pro Asn Thr Leu Lys Asn Thr
            35                  40                  45

Lys Asp Gln Ala Thr Val Asp Lys Leu Phe Gln Asp Leu Asp Ala Asp
    50                  55                  60

Lys Asp Gly Gln Val Asn Phe Asn Glu Phe Ile Ser Leu Val Ser Val
65                  70                  75                  80

Val Leu Asp Thr Ser His Lys Asn Thr His Lys Glu
                85                  90

<210> SEQ ID NO 3
<211> LENGTH: 94
<212> TYPE: PRT
<213> ORGANISM: Horse

<400> SEQUENCE: 3

Glu Lys Met Thr Lys Leu Glu Asp His Leu Glu Gly Val Ile Asn Ile
1               5                   10                  15

Phe His Gln Tyr Ser Ala Arg Val Gly His Phe Asp Thr Leu Ser Lys
            20                  25                  30

Gly Glu Leu Lys Gln Leu Ile Thr Arg Glu Leu Ala Asn Ser Ile Lys
        35                  40                  45

Asn Thr Lys Asp Lys Ala Thr Ile Asp Gln Ile Phe Gln Asp Leu Asp
    50                  55                  60

Ala Asp Lys Asp Gly Gln Val Ser Phe Asn Glu Phe Val Val Leu Val
65                  70                  75                  80

Cys Lys Val Leu Lys Thr Ala His Glu Asp Ile His Lys Glu
                85                  90

<210> SEQ ID NO 4
<211> LENGTH: 92
<212> TYPE: PRT
<213> ORGANISM: Bovine

<400> SEQUENCE: 4

Met Thr Lys Leu Glu Asp His Leu Glu Gly Ile Ile Asn Ile Phe His
1               5                   10                  15

Gln Tyr Ser Val Arg Val Gly His Phe Asp Thr Leu Asn Lys Arg Glu
            20                  25                  30

Leu Lys Gln Leu Ile Thr Lys Glu Leu Pro Lys Thr Leu Gln Asn Thr
        35                  40                  45

Lys Asp Gln Pro Thr Ile Asp Lys Ile Phe Gln Asp Leu Asp Ala Asp
    50                  55                  60

Lys Asp Gly Ala Val Ser Phe Glu Glu Phe Val Val Leu Val Ser Arg
65                  70                  75                  80

Val Leu Lys Thr Ala His Ile Asp Ile His Lys Glu
                85                  90

<210> SEQ ID NO 5
<211> LENGTH: 92
<212> TYPE: PRT
<213> ORGANISM: Artificial Seuquence
<220> FEATURE:
<223> OTHER INFORMATION: S100A12 mutant

<400> SEQUENCE: 5

Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Asn
    50                  55                  60

Gln Asp Glu Gln Val Asp Phe Gln Ala Phe Ile Ser Leu Val Ala Ile
65                  70                  75                  80

Ala Leu Lys Ala Ala His Tyr His Thr His Lys Glu
                85                  90

<210> SEQ ID NO 6
<211> LENGTH: 92
<212> TYPE: PRT
<213> ORGANISM: Artificial Sequence
<220> FEATURE:
<223> OTHER INFORMATION: S100A12 mutant

<400> SEQUENCE: 6

Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Ala
    50                  55                  60

Gln Asp Glu Gln Val Asp Phe Gln Glu Phe Ile Ser Leu Val Ala Ile
65                  70                  75                  80

Ala Leu Lys Ala Ala His Tyr His Thr His Lys Glu
            85                  90

<210> SEQ ID NO 7
<211> LENGTH: 92
<212> TYPE: PRT
<213> ORGANISM: Artificial Sequence
<220> FEATURE:
<223> OTHER INFORMATION: S100A12 mutant

<400> SEQUENCE: 7

Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Ala
    50                  55                  60

Gln Asp Glu Gln Val Asp Phe Gln Ala Phe Ile Ser Leu Val Ala Ile
65                  70                  75                  80

Ala Leu Lys Ala Ala His Tyr His Thr His Lys Glu
            85                  90

<210> SEQ ID NO 8
<211> LENGTH: 114
<212> TYPE: PRT
<213> ORGANISM: Human

<400> SEQUENCE: 8

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
            85                  90                  95

Gly Asp Glu Gly Pro Gly His His Lys Pro Gly Leu Gly Glu Gly
            100                 105                 110

Thr Pro

<210> SEQ ID NO 9
<211> LENGTH: 93
<212> TYPE: PRT
<213> ORGANISM: Human

<400> SEQUENCE: 9

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

```
Lys Gly Ala Asp Val Trp Phe Lys Glu Leu Asp Ile Asn Thr Asp Gly
    50              55                  60

Ala Val Asn Phe Gln Glu Phe Leu Ile Leu Val Ile Lys Met Gly Val
65              70                  75                  80

Ala Ala His Lys Lys Ser His Glu Glu Ser His Lys Glu
            85              90
```

COMPLEX-SPECIFIC STANDARDIZATION OF IMMUNOLOGICAL METHODS FOR THE QUANTIFICATION OF S100A12

CROSS-REFERENCE TO RELATED APPLICATIONS

This application claims priority to International Application No. PCT/EP2017/068100, filed on Jul. 18, 2017, which claims the benefit of foreign Application No. EP16180284.8 filed on Jul. 20, 2016, the content of which is incorporated by reference in its entirety. Also, the entire contents of the ASCII text file entitled "IPM0090US_Sequence_Listing.txt" created on Jan. 18, 2019, having a size of 8.04 kilobytes is incorporated herein by reference.

FIELD OF THE INVENTION

The present invention relates to mutants of S100A12 having at least one mutation in the high-affinity calcium binding hand or the low-affinity calcium binding hand or the zinc binding region. The present invention also relates to methods of detecting S100A12 dimers in a sample as well as methods of diagnosis using the S100A12 mutant of the invention, as well as to diagnostic compositions and kits comprising such an S100A12 mutant. The present invention further relates to a method of generating an antibody that specifically binds to an S100A12 dimer using the S100A12 mutant of the invention, as well as to an antibody that specifically binds to an S100A12 dimer.

BACKGROUND

Acute and chronic inflammations are still a major problem in clinical practice. Especially in chronic cases, the adaptation of the therapy is still the main problem. An overtreatment is associated with the risk of side effects and increased costs, while a sub therapy involves the risk of a new outbreak of inflammation or may be associated with long-term complications of uncontrolled inflammatory response. This problem has increased relevance with the introduction of so-called biologics (usually antibody-based therapies). While it is often possible to achieve remission with these drugs, it is unclear how long and at what dosage the treatment must be continued to treat. Accordingly, this group of drugs has become a large cost factor in our health care system. For these reasons, biomarkers as diagnostic tools that reliably reflect disease progression and detect particular subclinical residual activities of inflammation or even predict relapses are of particular importance. The calcium-binding protein S100A12 has been proposed as suitable and reliable biomarkers to indicate the course of an inflammatory disease. In particular, in rheumatoid arthritis and inflammatory bowel disease in which biologics are often applied for therapy, these biomarkers are clearly superior to conventional laboratory parameters and clinical scores. The general relevance of this biomarker is disclosed in WO 03/069341.

S100A12 (S100 calcium-binding protein A12) is a protein that in humans is encoded by the S100A12 gene. It is also known as calgranulin C. This protein is a member of the S100 family of proteins containing 2 EF-hand calcium-binding motifs. S100 proteins are localized in the cytoplasm and/or nucleus of a wide range of cells, and involved in the regulation of a number of cellular processes such as cell cycle progression and differentiation. This protein is proposed to be involved in specific calcium-dependent signal transduction pathways and its regulatory effect on cytoskeletal components may modulate various neutrophil activities.

As calcium-binding cytosolic molecules S100 proteins are characterized by two calcium-binding EF hands with different affinities for calcium connected by a central hinge region: a high affinity site at the C terminus (EF-hand II) and a low affinity site at the N terminus (EF-hand I). The EF-hand motifs have two α-helices flanking a central calcium-binding loop, thus resulting in a classical helix-loop-helix motif S100A12 proteins are usually only found in oligomeric states, such as dimers, tetramers, or hexamers. Further, these different oligomeric states appear to be related to different functional states. It is assumed that the dimeric form of S100A12 is particularly relevant for the diagnosis or assessment of the disease state.

However, when using e.g. conventional S100A12-ELISAs for quantification of these proteins in biological samples, which are based on diverse antibodies, at the moment it cannot be differentiated whether the measured values represent the dimer, tetramer, or hexamer form.

Accordingly, there is a need in the art for new means and methods which allow for a differentiation between S100A12 dimers and S100A12 tetramers or hexamers and an accurate detection of S100A12 dimers in a sample. Such a method would provide a precise diagnostic tool for the detection of a disease associated with S100A12 dimers. Moreover, such a method would allow for the recognition of the structural state of S100A12 proteins in order to reliably reflect the progression of an acute and chronic inflammatory disease. In particular, this method would allow for the exact quantification of the biologic active form of S100A12 complex. Moreover, even the detection of subclinical residual activities of inflammation at an early inflammatory state would be possible. The technical problem underlying the present application is thus to comply with this need. The technical problem is solved by providing the embodiments reflected in the claims, described in the description and illustrated in the examples and figures that follow.

SUMMARY OF THE INVENTION

The present invention discloses for the first time that S100A12 dimers having at least one mutation in the high- or low-affinity calcium binding region or the zinc binding region of S100A12 are well suited standards for use in a method of detecting S100A12 dimers in a sample. This is so, because these S100A12 dimers are no longer able to tetramerize or hexamerize and thus particularly useful for the reliable evaluation of the amount of S100A12 dimers in biological samples (e.g. those obtained from the respective patients).

The invention provides a mutant of S100A12 comprising at least one mutation in one of the following regions: the high-affinity calcium binding hand of S100A12 and/or the low-affinity calcium binding hand of S100A12 and/or the zinc binding region of S100A12. Such a mutant may be able to form S100A12 dimers but may not be able to form tetramers or hexamers.

The invention further provides a method for detecting an S100A12 dimer in a sample, wherein the method comprises detecting an S100A12 mutant according of the invention. In this method, wherein the S100A12 mutant may be used as a standard.

Also provided is a method for the diagnosis of a disease, wherein the method comprises detecting a S100A12 mutant of the invention and detecting an S100A12 in a sample obtained from a subject. In is understood that the S100A12 detected in the sample is preferably a dimeric S100A12. It is further understood that the disease is an inflammatory disease.

The invention further provides a method of monitoring the progression or regression of an acute or chronic inflammatory disease associated with an increased amount of S100A12 dimer in a subject. The method comprises (a) quantifying the amount of S100A12 dimer in a sample obtained from the subject using an S100A12 mutant of the invention and (b) comparing the amount of S100A12 dimer determined in (a) with the amount of S100A12 dimer in a sample that was obtained from the subject at an earlier date, wherein the result of the comparison of (b) provides an evaluation of the progression or regression of the inflammatory disease in the subject.

The invention further provides diagnostic compositions and kits comprising the S100A12 mutant of the invention. The invention also relates to the use of an S100S12 mutant of the invention in method of detecting an S100A12 dimer in a sample.

The invention further relates to a method of generating an antibody that specifically binds to dimeric S100A12. The invention further relates to an antibody that specifically binds to dimeric S100A12.

DETAILED DESCRIPTION OF THE INVENTION

The following description includes information that may be useful in understanding the present invention. It is not an admission that any of the information provided herein is prior art or relevant to the presently claimed inventions, or that any publication specifically or implicitly referenced is prior art.

The present invention is at least partly based on the surprising finding that S100A12 heterodimers comprising at least one mutation in the high- or low-affinity calcium binding hand or the zinc binding region do no longer form tetramers or hexamers and therefore can be applied as a reliable standard for the detection of S100A12 dimers in a sample. S100A12 dimers comprising at least one mutation in one of these regions can thus be considered as a stable S100A12 dimer standard.

S100A12 is a member of the calgranulin family. Other members of this family are S100A8/S100A9, which for heterodimers and tetramers under physiological conditions. For S100A8/S100A9, it has been demonstrated in the art that mutations in EF-hand II do not interfere with formation of S100A8/S100A9 heterodimers, but calcium-induced association to $(S100A8/S100A)_2$ tetramers is strictly dependent on a functional EF-hand II in S100A9. As shown by Leukert et al., J Mol Biol (2006), 359: 961-972, mutations within the C-terminal EF-hand of S100A9 (e.g. N69A, E79A, N69A+ E78A) destroy the high-affinity C-terminal calcium-binding site, leading to failure of tetramer formation in the presence of calcium. This is associated with a lack of functional activity of mutated S100A8/S100A9 complexes in promoting the formation of microtubules. On the other hand, formation of S100A8/S100A9 heterodimers is unaffected by the different mutations in the C-terminal EF-hand.

The inventors of the present invention have surprisingly found out that introducing corresponding mutations to S100A12 will similarly impair the protein's ability to form tetramers or hexamers, but will not influence the ability of S100A12 to form homodimers. The inventors of the present invention have further found out that for tetramerization or hexamerization of S100A12, not only calcium is needed, but also zinc. Consequently, the inventors of the present invention have surprisingly found that not only introducing a mutation to one of the calcium binding regions of S100A12 may impair tetramerization or hexamerization, but introducing a mutation to a zinc binding region of S100A12 may equally impair tetramerization or hexamerization of S100A12. The inventors of the present invention have further surprisingly found that such a S100A12 mutant may be useful for the detection of S100A12 in a sample. For example, the S100A12 mutant of the invention can be used as a standard for dimeric S100A12.

Accordingly, the S100A12 mutant of the present invention was found to be well suited for standardizing immunoassays (including inter alia established immunoassays that have been used for the detection of S100A12 and disease associated therewith, such as acute and chronic inflammatory diseases) and for detecting S100A12 dimers in a sample. This was unforeseeable since up to now available S100A12 detection assays (including the ones that are commercially available) are based on standards comprising an undefined mixture of dimeric, tetrameric, and hexameric forms, dependent on the calcium concentration in the medium. Accordingly, the methods described in the art are not appropriate to determine the amount of dimeric S100A12 complexes, but relate to the total amount of S100A12 irrespective of the multimerization grade (dimer, tetramer). Differentiation between different oligomeric states of S100A12 may however be important for diagnostic purposes, which especially holds true in the field of diagnostics. One prerequisite for such differentiation may be the availability of a S100A12 standard with a defined oligomeric state, i.e. where the oligomeric state does not depend on the calcium or zinc concentrations of the sample. A S100A12 mutant of the invention, which only forms dimers, may thus be useful as such a standard.

As figured out by the present inventors, commercially available quantitative ELISA use capture antibodies which do not differentiate between S100A12 dimers and tetramers or hexamers, probably due to the lack of a monoclonal AB which exclusively binds to S100A12 dimers but not to tetramers or hexamers. In fact, applying a human S100A12 dimer standard comprising the S100A12 of the invention in a commercially available S100A12 ELISA based on a buffer containing calcium leads to comparable standard values for both the commercial standard and the S100A12 dimer standard of the present invention. These results indicate that a differentiation between dimeric and tetrameric or hexameric complexes is not possible when using commercially available S100A12 ELISA. However, without wishing to be bound by theory, it is believed that under physiological conditions, there is equilibrium between the different oligomeric states of S100A12 (dimer, tetramer, hexamer). It is however further believed that only the dimer is physiologically active, while the tetramer or the hexamer are physiologically inactive. Hence, it is believed that only the level of the dimeric S100A12 is indicative for an inflammatory condition, which is why there is a need for a test that specifically identifies the dimeric S100A12 rather than detecting all oligomeric forms of S100A12. Accordingly, the S100A12 dimer standard of the present invention may be used to improve and/or standardize the respective immunoassay by providing a defined protein standard.

The present invention therefore relates to a S100A12 mutant comprising at least one mutation in one of the following regions: the high-affinity calcium binding hand of S100A12 and/or the low-affinity binding hand of S100A12 and/or the zinc binding region of S100A12.

The term "mutant" in reference to a nucleic acid or a polypeptide refers to the a nucleic acid or a polypeptide comprising an exchange, deletion, or insertion of one or more nucleotides or amino acids, respectively, compared to the "naturally" occurring nucleic acid or polypeptide, i.e. to a reference sequence that can be taken to define the wild-type. Out of the possible mutations, an exchange of an amino acid is preferred. For example, a reference sequence for a human S100A12 protein may the wild type human S100A12 protein set forth in SEQ ID NO: 01. Likewise, the terms "mutated" and "mutation" in reference to a nucleic acid or a polypeptide refers to an exchange, deletion, or insertion of one or more nucleotides or amino acids, respectively, compared to the "naturally" occurring nucleic acid or polypeptide.

S100A12 refers to an S100 calcium-binding protein A12, which is also known as calgranulin C. Exemplary S100A12 proteins are, among others, the human S100A12 with the UniProt accession number P80511 (version 2 of 23 Jan. 2007), the bovine S100A12 with the UniProt accession number P79105 (version 3 of 23 Jan. 2007), the pig S100A12 with the UniProt accession number P80310 (version 2 of 20 Feb. 2007), the rabbit S100A12 with the UniProt accession number O77791 (version 4 of 31 Oct. 2012), the dog S100A12 with the UniProt accession number J9PAQ5 (version 1 of 31 Oct. 2012), the sheep S100A12 with the UniProt accession number W5NQJ0 (version 1 of 16 Apr. 2014), the horse S100A12 with the UniProt accession number F6Z230 (version 1 of 27 Jul. 2011), or the chimpanzee S100A12 with the UniProt accession number H2Q027 (version 1 of 21 Mar. 2012). The term "S100A12" may optionally refer to a functional fragment of a S100A12 protein. A functional fragment of an S100A12 protein relates to proteins or peptides derived from any full-length S100A12 protein that is N-terminally and/or C-terminally shortened, i.e. lacking at least one of the N-terminal and/or C-terminal amino acids. Such a fragment comprises preferably at least about 70, preferably at least about 75, preferably at least about 80, preferably at least about 81, preferably at least about 82, preferably at least about 83, preferably at least about 84, preferably at least about 85, preferably at least about 86, preferably at least about 87, preferably at least about 88, preferably at least about 89, preferably at least about 90, preferably at least about 91 consecutive amino acids of the primary sequence of an S100A12 protein.

It is envisioned by the invention that such a mutation may not interfere with the S100A12 mutant's ability to form dimers. Hence, the S100A12 mutant of the invention may have the ability of forming dimers. However, due to the one or more mutation(s), it is envisioned that the S100A12 mutant of the invention may have a diminished ability to form tetramers or hexamers as compared to the wild type S100A12 protein, or may not be able to form tetramers or hexamers at all. Hence, the S100A12 mutant of the invention may exclusively exist as a dimeric complex. This is so, because the mutation may prevent the oligomerization of the dimer to a tetramer (i.e. it does not significantly tetramerize) or hexamer (i.e. it does not significantly hexamerize). "Significantly" means that a S100A12 mutant standard may still comprise up to 10%, preferably up to 5%, more preferably up to just 1%, even more preferably up to just 0.5% (w/w) impurity of S100A12 tetramers or hexamers when compared to the total amount of S100A12. The standard comprises in a most preferred embodiment no detectable impurity with S100A12 tetramers or hexamers.

The invention further contemplates that the S100A12 mutant of the invention may have a lower binding affinity to calcium as compared to the corresponding wild type S100A12 protein. By "lower binding affinity" it may be understood that the binding affinity is by factor of at least about 2, at least about 3, at least about 4, at least about 5, at least about 10, at least about 20, at least about 50, at least about 100, at least about 200, at least about 500, at least about 1000, at least about 2000, at least about 5000, or at least about 10000 lower than the corresponding wild type S100A12. The binding affinity may be expressed by a dissociation constant ($K_D$). It is understood that a lower $K_D$ value corresponds to a higher binding affinity. It is noted in this regard, the term "about" as used herein means within a deviation of 20%, such as within a deviation of 10% or within 5% of a given value or range.

The invention further contemplates that the S100A12 mutant of the invention may have a lower binding affinity to zinc as compared to the corresponding wild type S100A12 protein.

The S100A12 mutant of the invention may be a mutant of a mammalian S100A12 protein, preferably a mutant of a human S100A12, a canine S100A12, an equine S100A12, or a bovine S10012. The human S100A12 may have an amino acid sequence as set forth in SEQ ID NO: 01. The canine S100A12 may have an amino acid sequence as set forth in SEQ ID NO: 02. The equine S100A12 may have an amino acid sequence as set forth in SEQ ID NO: 03. The bovine S100A12 may have an amino acid sequence as set forth in SEQ ID NO: 04. It is most preferred that the S100A12 mutant of the invention is a mutant of a human S100A12, preferably as set forth in SEQ ID NO: 01.

As mentioned herein, an S100A12 protein comprises two calcium-binding EF hands with different affinities for calcium connected by a central hinge region: a high affinity site at the C terminus ("high affinity calcium binding hand" or "EF-hand II") and a low affinity site at the N terminus ("low affinity calcium binding hand" or "EF-hand I"). The high affinity calcium binding hand may refer to amino acid positions corresponding to amino acid positions 58 to 74 of the human S100A12 protein as set forth in SEQ ID NO: 01. The low affinity calcium binding hand may refer to amino acid positions corresponding to amino acid positions 16 to 34 of the human S100A12 protein as set forth in SEQ ID NO: 01. The inventors of the present application have identified that these amino acid positions of the high affinity calcium binding hand and the low affinity calcium binding hand may be particularly relevant for calcium binding and/or tetramerization or hexamerization of S100A12.

An S100A12 protein further has a binding region for a zinc molecule. Said binding region may be formed by amino acid positions corresponding to amino acid positions 14 to 27 and 83 to 92 of the human S100A12 protein as set forth in SEQ ID NO: 01.

It is also envisaged that the S100A12 mutant comprises mutations such as amino acid exchanges outside the mutated regions and/or modifications that are located within and/or outside the mutated regions that have been defined herein, as long as these further mutations/modifications do not significantly alter the S100A12 dimer structure. Thus, modifications and/or further alterations (e.g. truncations) are allowed as long as these modifications/alterations do not affect the dimer. It is particularly envisaged that the alterations and/or modifications do not affect the binding specificity of an antibody that is specific for the dimer. It is further envisaged that the S100A12 mutant can be modified but this modification or alteration should preferably not affect the epitope said antibody.

Consequently, the S100A12 mutant of the invention may comprise at least one mutation at an amino acid position corresponding to a position ranging from amino acid position 58 to amino acid position 74 of the human S100A12 as set forth in SEQ ID NO: 1; or an amino acid position corresponding to a position ranging from amino acid position 16 to amino acid position 34 of the human S100A12 as set forth in SEQ ID NO: 1, or an amino acid position corresponding to a position ranging from amino acid position 14 to amino acid position 27 or from amino acid position 83 to amino acid position 92 of the human S100A12 as set forth in SEQ ID NO: 1. Thus the S100A12 mutant of the invention may comprise a mutation at one or more amino acid positions corresponding to positions 58, 59, 60, 61, 62, 63, 64, 65, 66, 67, 68, 69, 70, 71, 72, 73, 74, 16, 17, 18, 19, 20, 21, 22, 23, 24, 25, 26, 27, 28, 29, 30, 31, 32, 33, 34, 14, 15, 83, 84, 84, 85, 86, 87, 88, 89, 90, 91, or 92.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids, but is rather to be viewed in the context of the circumjacent portion of the sequence. Accordingly, the position of a given amino acid in accordance with the disclosure which may be substituted may vary due to deletion or addition of amino acids elsewhere in a (mutant or wild-type) sequence. In this regard it is also noted that data base entries on a nucleic acid sequence of a protein may vary in their coverage of non-translated regions, thereby identifying different nucleic acid positions, even though the length of the coding region is unchanged/the same.

Thus, when a position is referred to as a "corresponding position" in accordance with the disclosure it is understood that nucleotides/amino acids may differ in terms of the specified numeral but may still have similar neighbouring nucleotides/amino acids. Such nucleotides/amino acids which may be exchanged, deleted or added are also included in the term "corresponding position".

Specifically, in order to determine whether an amino acid residue of the amino acid sequence of a S100A12 corresponds to a certain position in the amino acid sequence of a specific S100A12 protein, e.g. to human S100A12, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a known S100A12 protein may serve as "subject sequence" or "reference sequence", while the amino acid sequence of an S100A12 different from said reference sequence can serve as "query sequence".

The S100A12 mutant of the invention may preferably have a mutation at one or more amino acids that are involved in calcium binding or zinc binding. Preferably, these amino acids are involved in calcium or zinc binding of the dimeric S100A12 protein. Preferably, the side chains of these amino acids bind to calcium or zinc in the dimeric S100A12 protein. Amino acids of S100A12 that bind to calcium or zinc are for example disclosed in Moroz et al. (2003) Microscopy Research and Technique 60:581-592.

The S100A12 mutant of the invention may preferably comprise a mutation at 1, 2, 3, 4, 5, 6, 7, 8, 9, 10, 11, 12, or 13 amino acids at an amino acid corresponding to amino acid His16, Ser19, Lys22, His24, Asp26, Thr27, Glu32, Asp62, Asn64, Asp66, Glu73, His86, or His90 of human S100A12. Said mutation is preferably an amino acid exchange. Preferred positions that are mutated in the S100A12 mutant of the invention are Glu32, Asp62, Asn64, Asp66 or Glu73. Hence, the in the S100A12 mutant of the invention may comprise a mutation at 1, 2, 3, 4, or 5 amino acids positions corresponding to Glu32, Asp62, Asn64, Asp66 or Glu73 of human S100A12. For example, the present invention may contemplate an S100A12 mutant comprising a mutation at one of the following amino acids or sets of amino acids: Glu32; Asp62; Asn64; Asp66; Glu73; Glu32 and Asp62; Glu32 and Asn64; Glu32 and Asp66; Glu32 and Glu73; Asp62 and Asn64; Asp62 and Asp66; Asp62 and Glu73; Asn64 and Asp66; Asn64 and Glu73; Asp66 and Glu73; Glu32, Asp62 and Asn64; Glu32, Asp62 and Asp66; Glu32, Asp62 and Glu73; Glu32, Asn64, and Asp66; Glu32, Asn64, and Glu73; Glu32, Asp66 and Glu73; Asp62, Asn64, and Asp66; Asp62, Asn64, and Glu73; Asp62, Asp66, and Glu73; Asn64, Asp66, and Glu73; Glu32, Asp62, Asn64, and Asp66; Glu32, Asp62, Asn64, and Glu73; Glu32, Asn64, Asp66, and Glu73; Glu32, Asp62, Asp66, and Glu73; Asp62, Asn64, Asp66, and Glu73; or Glu32, Asp62, Asn64, Asp66, and Glu73.

As mentioned herein, the mutation may preferably be an amino acid exchange, preferably an amino acid exchange to glycine or alanine. Consequently, the S100A12 mutant of the invention may comprise a glycine or an alanine, preferably an alanine at 1, 2, 3, 4, 5, 6, 7, 8, 9, 10, 11, 12, or 13 amino acids at an amino acid corresponding to amino acid His16, Ser19, Lys22, His24, Asp26, Thr27, Glu32, Asp62, Asn64, Asp66, Glu73, His86, or His90 of human S100A12. It may comprise a glycine or an alanine, preferably an alanine at 1, 2, 3, 4, or 5 amino acids positions corresponding to Glu32, Asp62, Asn64, Asp66 or Glu73 of human S100A12. For example, the present invention may contemplate an S100A12 mutant comprising a glycine or an alanine, preferably an alanine at one of the following amino acids or sets of amino acids: Glu32; Asp62; Asn64; Asp66; Glu73; Glu32 and Asp62; Glu32 and Asn64; Glu32 and Asp66; Glu32 and Glu73; Asp62 and Asn64; Asp62 and Asp66; Asp62 and Glu73; Asn64 and Asp66; Asn64 and Glu73; Asp66 and Glu73; Glu32, Asp62 and Asn64; Glu32, Asp62 and Asp66; Glu32, Asp62 and Glu73; Glu32, Asn64, and Asp66; Glu32, Asn64, and Glu73; Glu32, Asp66 and Glu73; Asp62, Asn64, and Asp66; Asp62, Asn64, and Glu73; Asp62, Asp66, and Glu73; Asn64, Asp66, and Glu73; Glu32, Asp62, Asn64, and Asp66; Glu32, Asp62, Asn64, and Glu73; Glu32, Asn64, Asp66, and Glu73; Glu32, Asp62, Asp66, and Glu73; Asp62, Asn64, Asp66, and Glu73; or Glu32, Asp62, Asn64, Asp66, and Glu73. It is understood that in cases where more than one amino acid is exchanged, the amino acids may be exchanged to any combination of amino acids, preferably any combination of glycine or alanine. It is also contemplated that in cases where more than one amino acid is exchanged, the amino acids may all be exchanged to the same amino acids. Preferably, all exchanged amino acids may be exchanged to glycine or alanine, preferably to alanine. Particularly preferred are S100A12 mutants that comprise an alanine at an amino acid position corresponding to position Asn64 or Glu73 of human S100A12. Preferred are S100A12 mutants wherein the position corresponding to Glu73 of human S100A12 is exchanged to alanine, even more preferred are mutants having only this substitution. Preferred are also S100A12 mutants wherein the position corresponding to Asn64 of human S100A12 is exchanged to alanine, even more preferred are mutants having only this substitution. Preferred are also S100A12 mutants, where both positions corresponding to Asn64 and Glu73 of human S100A12 are exchanged to alanine, even more preferred are mutants having only this substitution.

The S100A12 mutant of the invention may have a sequence identity of at least about 75%, preferably at least about 80%, preferably at least about 85%, preferably at least about 88%, preferably at least about 90%, preferably at least about 95%, preferably at least about 98%, or preferably at least about 99% as compared to the sequence of the corresponding wild type S100A12 protein. Preferably, the S100A12 mutant of the invention may have a sequence identity of at least about 75%, preferably at least about 80%, preferably at least about 85%, preferably at least about 88%, preferably at least about 90%, preferably at least about 95%, preferably at least about 98%, or preferably at least about 99% as compared to the sequence of wild type human S100A12 as set forth in SEQ ID NO: 01.

By "sequence identity" or "identity is meant a property of sequences that measures their similarity or relationship. Identity is measured by dividing the number of identical residues by the total number of residues and gaps and multiplying the product by 100. Preferably, identity is determined over the entire length of the sequences being compared. "Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25:3389-3402), Blast2 (Altschul, et al. (1990) J. Mol. Biol. 215:403-410), and Smith-Waterman (Smith, et al. (1981) J. Mol. Biol. 147:195-197).

The S100A12 mutant of the invention may have a sequence identity of at least about 75%, preferably at least about 80%, preferably at least about 85%, preferably at least about 88%, preferably at least about 90%, preferably at least about 95%, preferably at least about 98%, preferably at least about 99%, or about 100% as compared to the sequence of the of the S100A12 mutant set forth in SEQ ID NO: 05. The S100A12 mutant of the invention may have a sequence identity of at least about 75%, preferably at least about 80%, preferably at least about 85%, preferably at least about 88%, preferably at least about 90%, preferably at least about 95%, preferably at least about 98%, preferably at least about 99%, or about 100% as compared to the sequence of the of the S100A12 mutant set forth in SEQ ID NO: 06. The S100A12 mutant of the invention may have a sequence identity of at least about 75%, preferably at least about 80%, preferably at least about 85%, preferably at least about 88%, preferably at least about 90%, preferably at least about 95%, preferably at least about 98%, preferably at least about 99%, or about 100% as compared to the sequence of the of the S100A12 mutant set forth in SEQ ID NO: 07.

The S100A12 mutant of the invention may optionally comprise a peptide tag, which may be useful for purification of the S100A12 mutant. A "peptide tag" as used herein may refer to a polypeptide fused to the S100A12 mutant. Such a polypeptide may preferably be fused N-terminally of the S100A12 mutant or C-terminally of the S100A12 mutant. The peptide tag preferably consists of a polypeptide chain of 1 to 100 amino acids, preferably of 1 to 50 amino acids, preferably of 1 to 40 amino acids, preferably of 1 to 30 amino acids, preferably of 1 to 25 amino acids, preferably of 1 to 20 amino acids, preferably of 1 to 15 amino acids, preferably of 1 to 10 amino acids. Such a peptide tag may e.g. be useful for the purification of the S100A12. As an illustrative example, such a tag may be selected from the group consisting of an oligohistidine tag, a strep-tag, a strep-tag II, a myc-tag, a FLAG tag, and an HA tag. Since the peptide tag may be seen as an additional element fused to the S100A12 core structure, one of ordinary skill in the art may understand that a peptide tag is not taken into account when determining the percentage sequence identity between a given S100A12 mutant and a reference S100A12, e.g. one of SEQ ID NO: 1-9. Instead, it may be understood that only that part of the S100A12 mutant, that aligns to the reference S100A12 when using BLAST align (blast.ncbi.nlm.nih.gov) is used for the calculation of sequence identity, while the amino acids, preferably those at the N- or C-terminus, that do not align with said reference S100A12 will be considered to be absent from the given S100A12 mutant for calculating the percentage sequence identity between the given S100A12 mutant and the reference S100A12.

The present invention also envisages methods and assays that preferably employ the S100A12 mutant of the invention. The S100A12 mutant of the invention may be used as a standard, e.g. as standard for dimeric S100A12.

It is envisioned that the S100A12 mutant standard of the present invention may be used in a detection method or assay exclusively detecting S100A12 dimers without detecting S100A12 tetramers or hexamers. Hence, the method or assay may allow for a specific quantification of S100A12 dimers in a sample. Accordingly, the S100A12 mutant may be employed in a method of diagnosing an inflammatory disease, allowing for the accurate detection of pro-inflammatory dimers, which seem to be more relevant for assessing the stage of an inflammatory disease in vivo. Thus, the means and methods of the present invention allow for detecting, diagnosing, monitoring etc. an acute and chronic inflammatory disease.

The term "detecting" when used herein includes variations like determining, qualifying, semi-qualifying or, as the case may be, diagnosing etc. The term "detect" or "detecting", as well as the term "determine" or "determining" when used in the context of a biomarker refers to any method that can be used to identify the presence of a protein/polypeptide released or expressed by a cell. In some embodiments the method of detecting an S100A12 dimer in a sample may be a method of detecting the level (quantitative or semi-quantitative) of S100A12, by comparing the level of S100A12 dimer in the sample with the level of S100A12 dimer standard. The methods of the present invention are preferably in vitro methods.

As described above, the present invention relates to the use of the S100A12 mutant as defined herein in a method of detecting S100A12 dimers in a sample. In this context, it is also envisaged to use the S100A12 mutant for the standardization of established detection methods which do not differentiate between S100A12 dimer and tetramers or hexamers, but detect the total amount of S100A12 in a sample. In this regard, established detection methods can also be compared using on the one hand the commercial standards and on the other hand the S100A12 mutant of the present invention as a dimer standard. Furthermore, the S100A12 mutant can be used in displacement assays. In some embodiments the detecting methods are quantitative immunoassays such as quantitative enzyme-linked immunosorbent assays (ELISAs). Accordingly, the present invention also provides for a method of standardizing a quantitative S100A12 immunoassay by using the S100A12 mutant of the present invention as protein standard in said immunoassay.

In a preferred embodiment the quantitative ELISA is a quantitative sandwich ELISA comprising the following steps:
(i) pre-coating a microplate with a monoclonal capture antibody capable of binding S100A12,
(ii) optionally contacting the pre-coated capture antibody with the sample to be analyzed and the standard comprising the S100A12 mutant as defined in the claims,
(iii) optionally washing away unbound sample and standard,
(iv) optionally contacting bound sample and standard with an enzyme-conjugated detecting antibody,
(v) optionally washing away free amounts of the detecting antibody,
(vi) optionally contacting the bond detecting antibody with the substrate of the conjugated enzyme,
(vii) optionally finishing the enzymatic reaction,
(viii) optionally photometrically determining the absorbance of the sample and the standard, and
(ix) optionally determining the amount of S100A12 dimer in the sample by comparing the absorbance with the absorbance of the standard.

The term "sample" when used herein relates to a material or mixture of materials, typically but not necessarily in liquid form, containing one or more analytes of interest. Preferably, the sample of the present invention is a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. The samples described herein include but are not limited to a stool sample, a blood sample, a serum sample, a plasma sample, a urine sample, a tissues extract sample or a cell culture sample, a stool sample, plasma sample or a serum sample being preferred. Biological samples from a subject may be obtained by an individual undergoing a self-diagnostic test (e.g., blood glucose monitoring) or by a trained medical professional through a variety of techniques including, for example, aspirating blood using a needle or scraping or swabbing a particular area. Methods for collecting various biological samples are well known in the art.

The term "subject" as used herein, also addressed as an individual, refers to a mammalian organism including a human or a non-human animal. Thus, the methods, uses and compositions described in this document are generally applicable to both human and non-human animals. As explained above, a sample may be analyzed that has been obtained from said subject, which is typically a living organism. Where the subject is a living human who may receive treatment or diagnosis for a disease or condition as described herein, it is also addressed as a "patient".

The S100A12 dimer has been proposed as a suitable and reliable biomarker to indicate the course of an inflammatory disease. The term "biomarker" is defined as a physical sign or laboratory measurement that occurs in association with a natural or pathological process, and that has putative diagnostic and/or prognostic utility. More precisely, the term "biomarker" may comprise a protein or a gene encoding a protein/peptide, which is expressed at a lower or higher level by a cell under different cellular conditions. In the present disclosure, said biomarker is preferably expressed and released by a subject under native and/or pathological conditions, such as inflammatory conditions. The biomarker described herein is usually expressed and released by an immune cell, in particular neutrophils, early differentiation stage of monocytes, keratinocytes and epithelial cells. Said biomarker is preferably S100A12 which generally exists as dimer or tetramer or hexamer depending on the amount of calcium at the release site. In the present invention, measuring the level of the dimeric complex of said biomarkers can be used for diagnosing and/or monitoring an acute or chronic inflammatory disease.

In the context of the present invention, the sample as described herein may be a sample from a subject suffering from an acute or chronic inflammatory disease. The acute or chronic inflammatory disease is essentially an inflammatory disease associated with an increased amount of S100A12 dimer. This disease may be selected from rheumatoid arthritis, juvenile idiopathic arthritis, psoriatic arthritis, immune reconstituation inflammatory syndrome (IRIS), sepsis, systemic inflammatory response syndrome (SIRS), pneumonia, osteomyelitis, autoinflammatory syndromes, hyperzincemia, systemic inflammation, atherosclerosis, acute coronary syndrome, myocardial infarction, Crohn's disease, colitis ulcerosa, glomerulonephritis (SLE), diabetes, an inflammatory skin disease, psoriasis, inflammatory bowel disease, vasculitis, allograft rejection, glomerulonephritis, systemic lupus erythematosus, pancreatitis, a cancer, dermatomyositis and polymyositis, multiple sclerosis, allergies, autoimmune diseases, cardiovascular diseases, infections, pulmonary inflammation, systemic onset juvenile idiopathic arthritis (SOJIA), acute lung injury (ALI) and its most severe form, acute respiratory distress syndrome (ARDS).

As described herein, commercially available S100A12 ELISAs do not differentiate between S100A12 dimer and the tetramer or hexamer, because the capture antibody used in these assays may equally binds to all forms. Moreover, these assays miss a defined protein standard, and the dimer-tetramer/hexamer ratio is strictly dependent on the amount of calcium or zinc in the buffer. Thus, the S100A12 mutant of the present invention may be well suited to standardize these commercially available S100A12 ELISAs by providing a defined protein standard. Accordingly, the present invention also provides for a method of detecting S100A12 in a biological sample, the method comprising the use of a S100A12 mutant of the invention. It is understood that the method of detection disclosed herein may be performed in the presence of a buffer. Suitable buffers are known in the art and may comprise HEPES, phosphate, or TRIS, e.g. in an amount of about 1 mM to about 100 mM, preferably about 5 mM to about 50 mM, preferably about 10 mM to about 40 mM, preferably about 10 mM to about 30 mM. The buffer may also comprise a (further) salt, such as NaCl. The salt may be in an amount of about 1 mM to about 500 mM, preferably about 10 mM to about 200 mM, preferably about 50 mM to about 180 mM, preferably about 100 mM to about 150 mM. The pH of the buffer is preferably in the range of about 5 to about 9, preferably about 6 to about 8.5, preferably about 7 to about 8, preferably about 7.1, about 7.2, about 7.3, about 7.4, about 7.5, about 7.6, about 7.7, about 7.8, about 7.9.

According to the present invention, the S100A12 mutant as defined herein may further be used in a method of detecting S100A12 dimers in a sample. These methods are based on a distinction between the dimeric and tetrameric or hexameric S100A12 complex. In this context, monoclonal capture antibodies are used which are capable of binding S100A12 dimers but no S100A12 tetramers or S100A12 hexamers. This necessarily implies that the antibody has a binding specificity to an epitope which is freely accessible on the S100A12 dimer, but not available in the tetrameric or hexameric form. As an illustrative example, the capture antibody may be an antibody having a binding specificity to an epitope of a mammalian S100A12 protein, wherein the epitope is within the range of the amino acid positions that correspond to positions 58 to position 74 of the human S100A12 with the UniProt accession number P80511 (version 2 of 23 Jan. 2007, SEQ ID NO: 01).

The method of quantifying S100A12 dimers may further comprise the step of comparing the amount of S100A12 dimers with the total amount of S100A12. The term "total amount" as used herein represents the sum of S100A12 dimers and tetramers and hexamers in a sample to be analyzed. This comparison will be well suited to determine the amount of S100A12 tetramers and hexamers in a sample and to assess the ratio between dimers and tetramers/hexamers. Accordingly, the present invention also relates to the use of the S100A12 mutant as defined herein in a method of comparing the amount of S100A12 dimers and tetramers/hexamers in a sample. Since in healthy subjects the proteins S100A12 are mainly present in the form of inactive tetramers or hexamers, the ratio between dimer and tetramer/hexamer will be appropriate for monitoring the progression or regression of an inflammatory disease associated with an increased amount of S100A12 dimer. A shift towards the S100A12 dimer may indicate the progression of an inflammatory disease, whereas a shift towards the S100A12 tetramer/hexamer may indicate a regression of an inflammatory disease. The total amount of S100A12 can be determined by any of the commercially available ELISAs described herein or by an alternative method. The skilled artisan is aware of the variety of techniques used for protein quantification such as photometric or chromatographic methods.

The present invention also provides a kit comprising the S100A12 mutant of the present invention. The kit is preferably for use in diagnosis. The kit of the invention may comprise a binding molecule which specifically binds to S100A12. The kit preferably provides components for carrying out an ELISA or immunochromatographic technique. According to some embodiments, the term "kit" when used herein refers to an assembly of useful compounds and other means like solid support plates or test stripes for detecting S100A12 in a mammalian sample. A kit therefore may include the S100A12 mutant and/or a composition comprising the S100A12 mutant of the present invention. As an illustrative example, such a kit may include a device having an immobilized capture antibody and other useful reagents like wash reagent, as well as detector reagent and the S100A12 mutant of the present invention. Other components such as buffers, controls, and the like, known to those skilled in art, may be included in such test kits. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample. The present kit may further include instructions for carrying out one or more methods of the present invention, including instructions for using a standard and/or composition comprising the S100A12 mutant of the present invention that is included with the kit. The diagnostic kit may comprise a monoclonal antibody binding to S100A12 dimers, tetramers, and hexamers. The diagnostic kit may comprise a monoclonal antibody exclusively binding to S100A12 dimers but not to tetramers or hexamers. The antibodies used in said kit can be present in bound or soluble form.

The invention further relates to a diagnostic composition comprising the S100A12 mutant of the present invention. The diagnostic composition may comprise a mixture of a binding molecule which specifically binds to S100A12 and chemical reagents. The binding molecule is preferably a monoclonal antibody binding to S100A12 dimers, tetramers, and hexamers, or a monoclonal antibody exclusively binding to S100A12 dimers. The antibody is preferably present in soluble form.

In the context of the present invention, the S100A12 mutant, the kit comprising said S100A12 mutant or the diagnostic composition comprising said S100A12 mutant may be used in a method of diagnosing an acute or chronic inflammatory disease in a human subject. Accordingly, a method of diagnosing an acute or chronic inflammatory disease in a subject is also provided herein. In this context the S100A12 mutant, the kit comprising said standard or the diagnostic composition comprising said standard are preferably used for diagnosing whether a subject is suffering from any of the acute or chronic inflammatory disease described herein. Accordingly, a sample taken from said subject is analyzed using the S100A12 mutant, the kit comprising said S100A12 mutant or the diagnostic composition comprising said S100A12 mutant according to the present invention. The sample may be any of the samples as described herein.

The method of diagnosing an acute or chronic inflammatory disease in a subject may comprises a) quantifying the amount of S100A12 dimer in a sample taken from said subject by using the S100A12 mutant of the present invention and b) comparing the amount of S100A12 dimer as determined in a) to reference data from a subject known to not suffer from an acute or chronic inflammatory disease. A significant increased amount of S100A12 dimer as compared to the reference data may indicate that the subject suffers from an acute or chronic inflammatory disease. No significant deviation in the amount of S100A12 dimer as compared to the reference data may indicate that the subject does not suffer from an acute or chronic inflammatory disease.

The acute or chronic inflammatory disease may essentially be an inflammatory disease associated with an increased amount of S100A12 dimer. This disease may be selected from rheumatoid arthritis, juvenile idiopathic arthritis, psoriatic arthritis, immune reconstituation inflammatory syndrome (IRIS), sepsis, systemic inflammatory response syndrome (SIRS), pneumonia, osteomyelitis, autoinflammatory syndromes, hyperzincemia, systemic inflammation, atherosclerosis, acute coronary syndrome, myocardial infarction, Crohn's disease, colitis ulcerosa, glomerulonephritis (SLE), diabetes, an inflammatory skin disease, psoriasis, inflammatory bowel disease, vasculitis, allograft rejection, glomerulonephritis, systemic lupus erythematosus, pancreatitis, a cancer, dermatomyositis and polymyositis, multiple sclerosis, allergies, autoimmune diseases, cardiovascular diseases, infections, pulmonary inflammation, systemic onset juvenile idiopathic arthritis (SOJIA), acute lung injury (ALI) and its most severe form, acute respiratory distress syndrome (ARDS).

Moreover, detecting the amount of S100A12 dimer in a sample by using the S100A12 mutant of the present invention can be used to define or evaluate the specific state of an acute or chronic inflammatory disease. Depending on the level of pro-inflammatory S100A12 dimer in a subject, the disease can be defined or evaluated as to be in a state of progression or remission. Moreover, also the risk of relapse during remission can be predicted or the efficacy of novel therapeutics in treatment of inflammatory diseases such as antibody-based therapies can be evaluated. Evaluating the efficacy of anti-inflammatory compounds refers to the assessment of whether or not a patient suffering from an inflammatory disease is responsive to said therapeutic compound. In this context, the amount of S100A12 in a sample from a subject will be predictive to assess if the therapy is effective or not. Thus, the amount of S100A12 dimer in a sample from said patient has to be compared with the amount of S100A12 dimer in a sample from said patient determined at an earlier date, preferably before initiation of treatment. A significantly increased amount of S100A12 dimer as compared to the reference data indicates a progression of the inflammatory disease associated with an increased amount of S100A12 dimer in said patient. No change or a decreased amount of S100A12 dimer as compared to the reference data indicates no progression or a regression of the inflammatory disease associated with an increased amount of S100A12 dimer in said patient. This principle is equally applicable for the evaluation of the progression of an inflammatory disease. Accordingly, the present invention further relates to a method of evaluating the progression of an inflammatory disease in a patient suffering from an acute or chronic inflammatory disease. Such evaluation may help an attending physician to obtain the appropriate information to set the appropriate therapy conditions for the treatment of the respective inflammatory disease. Also a method for evaluating whether a subject may be of a risk to develop an inflammatory disease is comprised by the present invention.

Additionally, the progression of an acute or chronic inflammatory disease in a patient can be monitored. Monitoring the progression indicates that the amount of S100A12 dimers in said patient is repeatedly determined during a certain period of time, either regularly or occasionally. The method for monitoring the progression of a disease in a patient can be a short-term monitoring or a long-term monitoring. Preferably, the amount of S100A12 dimer in a sample taken from said patient is quantified by any of the methods described herein. The amount of S100A12 dimer may further be compared to a reference sample from said patient quantified at an earlier date, wherein the result of the comparison provides an evaluation of the progression of the inflammatory disease. A significantly increased amount of S100A12 dimer as compared to the reference data may indicate a progression of the inflammatory disease, wherein no change or a decreased amount of S100A12 dimer as compared to the reference data may indicate no progression or a regression of the inflammatory disease.

It is understood that the methods described herein are preferably in vitro methods.

The invention also envisages the use of the S100A12 mutant in a method for generation, selection, and/or maturation etc. of antibodies or similar binding scaffolds, that are specific for an S100A12 dimer but do not bind or do not essentially bind to tetrameric or hexameric S100S12, which are therefore superior to the antibodies that bind to dimeric S100A12 and tetrameric or hexameric S100A12 (in terms of the detection of the S100A12 dimer) that are presently employed in commercially available immunoassays. Commercially available assays within the context of the present invention include but are not limited to quantitative S100A12 ELISA from e.g. BioVendor, R&D Systems, BosterBio, Creative Diagnostics, ALPCO, Abnova Corporation, LifeSpan BioSciences, to name some.

Methods of generation, selection and maturation of antibodies or similar binding scaffolds to a given target are well known to a skilled person. Having determined the amino acids (or amino acid regions) which are buried (non-solvens accessible) in the tetramer/hexamer but free in the homodimers of S100A12 (e.g. by computer-based simulations using the known 3D-coordinates of S100A12) it is possible to develop specific antibodies against these regions by using peptidic sequences of this region(s) and standard methods of monoclonal or polyclonal antibody generation. Such a region may be the amino acid positions that correspond to positions 58 to position 74 of the human S100A12 set forth in SEQ ID NO: 01

The present invention also relates to an antibody that is obtainable of any of the methods of generation, selection, and/or maturation of the present invention. It will be understood that this antibody may bind to the S100A12 dimer but does not bind or does not essentially bind to the tetramer or the hexamer. This is so, because its epitope to which the antibody binds is preferably located in a region that is not accessible for the antibody once the dimer tetramerizes or hexamerizes. In is envisioned that the antibody preferably binds to an epitope that is within the range of the amino acid positions that correspond to positions 58 to position 74 of the human S100A12 set forth in SEQ ID NO: 01. "Does not essentially bind" in this context may be understood such that the antibody have a binding affinity for tetrameric and hexameric S100A12, which is each at least about 10 fold lower than its binding affinity to dimeric S100A12, preferably at least about 20 fold lower, preferably at least about 30 fold lower, preferably at least about 40 fold lower, preferably at least about 50 fold lower, preferably at least about 100 fold lower, preferably at least about 200 fold lower, preferably at least about 300 fold lower, preferably at least about 400 fold lower, preferably at least about 500 fold lower, preferably at least about 1000 fold lower. Methods of the invention may comprise the use of said antibody.

The term "antibody" refers to a molecule in which the structure and/or function is/are based on the structure and/or function of an antibody, e.g. of a full-length or whole immunoglobulin molecule. An antibody construct is hence capable of binding to its specific epitope or antigen. Furthermore, an antibody construct according to the invention comprises the minimum structural requirements of an antibody which allow for the epitope binding. This minimum requirement may e.g. be defined by the presence of at least the three light chain CDRs (i.e. CDR1, CDR2 and CDR3 of the VL region) and/or the three heavy chain CDRs (i.e. CDR1, CDR2 and CDR3 of the VH region). The antibodies on which the constructs according to the invention are based include for example monoclonal, recombinant, chimeric, deimmunized, humanized and human antibodies. Within the definition of "antibody" according to the invention are full-length or whole antibodies including camelid antibodies and other immunoglobulin antibodies generated by biotechnological or protein engineering methods or processes. These full length antibodies may be for example monoclonal, recombinant, chimeric, deimmunized, humanized and human antibodies. Also within the definition of "antibody constructs" are fragments of full-length antibodies, such as VH, VHH, VL, (s)dAb, Fv, Fd, Fab, Fab', F(ab')2 or "r IgG" ("half antibody"). Antibodies according to the invention may also be modified fragments of antibodies, also called antibody variants, such as scFv, scFab, Fab2, Fab3, diabodies, single chain diabodies, "minibodies" exemplified by a structure which is as follows: (VH-VL-CH3)2, (scFv-CH3)2 or (scFv-CH3-scFv)2, and single domain antibodies such as nanobodies or single variable domain antibodies comprising merely one variable domain, which might be VHH, VH or VL, that specifically bind an antigen or epitope independently of other V regions or domains.

It is to be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the methods and uses described herein. Such equivalents are intended to be encompassed by the present invention.

Throughout this specification and the claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "consisting", "consisting of" and "consisting essentially of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

Several documents are cited throughout the text of this disclosure. Each of the documents cited herein (including all patents, patent applications, scientific publications, manufacturer's specifications, instructions, etc.), are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

BRIEF DESCRIPTION OF THE DRAWINGS

FIG. 1: Sequence alignment between human S100A12 (SEQ ID NO: 01) and human S100A9 (SEQ ID NO: 08). Positions involved in the complexation of $Ca^{2+}$ are highlighted.

FIG. 2: Multiple sequence alignment between human S100A12 (SEQ ID NO: 01), canine S100A12 (SEQ ID NO: 02), equine S100A12 (SEQ ID NO: 03), and bovine S100A12 (SEQ ID NO: 04). Positions involved in the complexation of $Ca^{2+}$ are highlighted in grey, positions involved in the complexation of $Zn^{2+}$ are depicted in bold italic letters.

FIG. 3: Mutants of human S100A12. FIG. 3A shows the amino acid sequence of a Glu73→Ala mutant of human S100A12 (SEQ ID NO: 05). FIG. 3B shows the amino acid sequence of an Asn64→Ala mutant of human S100A12 (SEQ ID NO: 06). FIG. 3C shows the amino acid sequence of an Asn64→Ala, Glu73→Ala mutant of human S100A12 (SEQ ID NO: 07).

FIG. 8: Glycerol centrifugation of S100A12 proteins. Wild type (wt) and mutant recS100A12 complexes were loaded on a 15% glycerol solution in the presence of either EGTA or $Ca^{2+}$ or $Zn^{2+}$ or $Ca^{2+}/Zn^{2+}$. Buffer conditions were 20 mM HEPES, 140 mM NaCl, pH 7.4. After centrifugation, successive fractions of the gradients were analyzed by the colorimetric assay Bradford. In the presence of EGTA wt and mutant complexes showed an almost identical distribution centered in the low density fractions of the gradient. Addition of calcium or zinc alone induced no shift for wtS100A12 to higher glycerol fractions. Addition of calcium plus zinc induced a marked shift for wtS100A12 to higher glycerol fractions, whereas for the mutant complex recS100A12(E73A) no shift was observed.

EXAMPLES

The following examples illustrate the invention. These examples should not be construed as to limit the scope of this invention. The examples are included for purposes of illustration and the present invention is limited only by the claims.

Figures 4, 5:
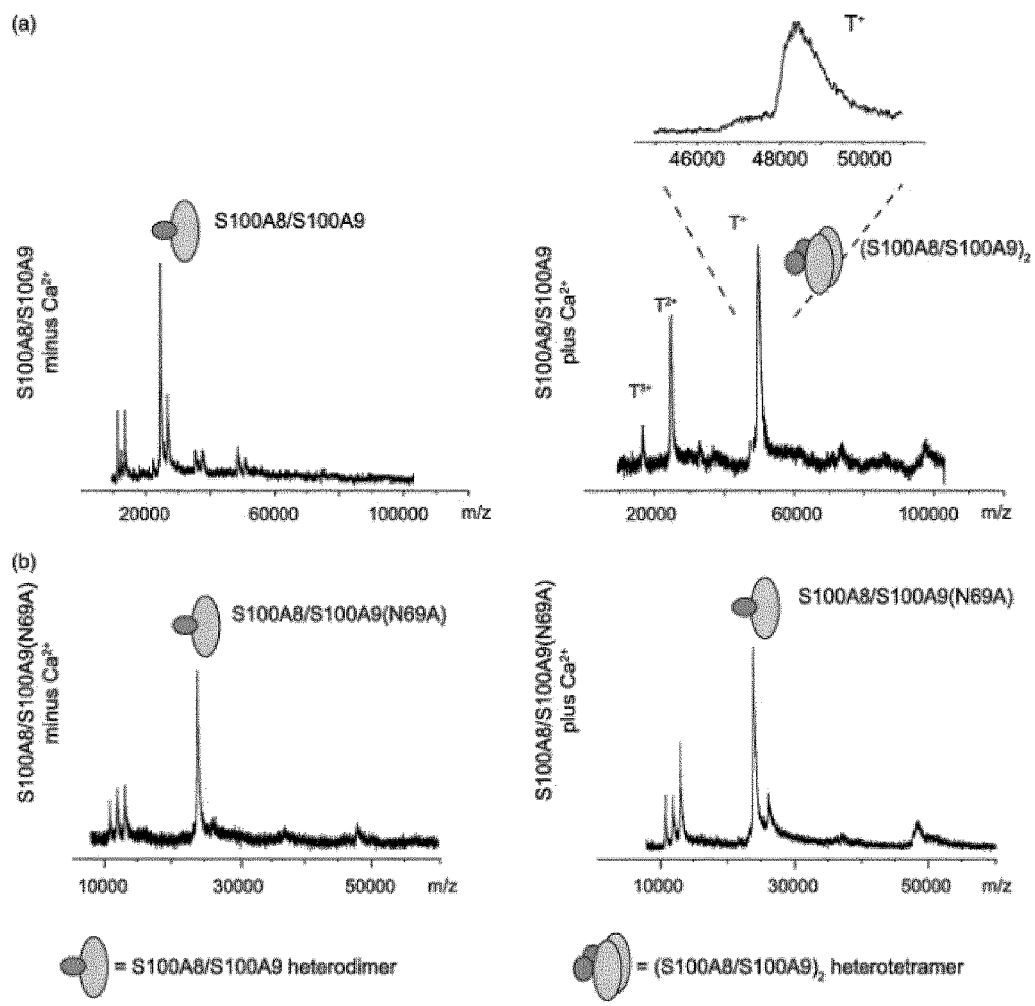
FIG. 4: Molecular masses determined by ESI-MS. The molecular masses of the recombinant S100A8 and S100A9 proteins are determined by ESI-MS under denaturing conditions and compared with their theoretical calculated masses. S100A8 refers to human S100A8 protein of Uniprot accession no. P05109 (version 1 as of 1 Jan. 1988, SEQ ID NO: 09). S100A9 refers to human S100A9 protein of Uniprot accession no. P06702 (version 1 as of 1 Jan. 1988, SEQ ID NO: 08). S100A9 (N69A) refers to a mutant of human S100A9 having a single Asn69→Ala substitution. S100A9 (E78A) refers to a mutant of human S100A9 having a single Glu78→Ala substitution. S100A9 (N69A+E78A) refers to a mutant of human S100A9 having a double Asn69→Ala and Glu78→Ala substitution.
FIG. 5: MALDI mass spectra in the absence and presence of calcium under native solvent conditions. (a) MALDI mass spectra of recS100A8/S100A9 wt complexes in the absence (left) and presence (right) of calcium using 2,6-dihydroxy-acetophenone as matrix. The mass spectra between m/z 20,000 and 100,000 together with an inset between m/z 46,000 and 50,000 are shown. $T^+$, singly charged; $T^{2+}$, doubly charged; $T^{3+}$, triply charged tetramer. (b) MALDI mass spectra of recS100A8/S100A9(N69A) mutant complexes in the absence (left) and presence (right) of calcium. RecS100A8/S100A9(E78A) and recS100A8/S100A9(N69A+E78A) showed almost identical results (data not shown).

Example 1: Differentiation Between S100A8/S100A9 Heterodimers and Teteramers Using MALDI-MS and ESI-MS Electrospray ionization mass spectrometry (ESI-MS) confirms the theoretically calculated masses without the N-terminal methionine (SwissProt) for mutated and non-mutated recombinant S100A8/S1009 proteins (FIG. 4).

S100A8 and S100A9 exist as heterodimers in the absence of calcium, and these heterodimeric complexes associate to (S100A8/S100A9)$_2$ tetramers upon calcium-binding. FIG. 5(a) shows the matrix-assisted laser desorption/ionisation mass spectrometry (MALDI-MS) spectra of the recS100A8/ S100A9 wt proteins. In the absence of calcium, samples show intense signals of singly charged heterodimers. In contrast, in the presence of Ca2+ wt S100A8/S100A9 show a base peak in first shot spectra that corresponds to a singly charged heterotetramer (T+: 48 kDa) composed of two molecules recS100A8 and two molecules of recS100A9, respectively. Other prominent signals are detected at molecular masses of around 24 kDa and 16 kDa, representing doubly charged (T2+) or triply charged (T3+) tetramers in accordance with results reported earlier for the native proteins purified from human granulocytes. The number of Ca2+ bound to the tetramers was calculated from the difference between the observed masses of the tetramers and the sum of the calculated theoretical molecular masses of the monomeric components.

Figure 6:
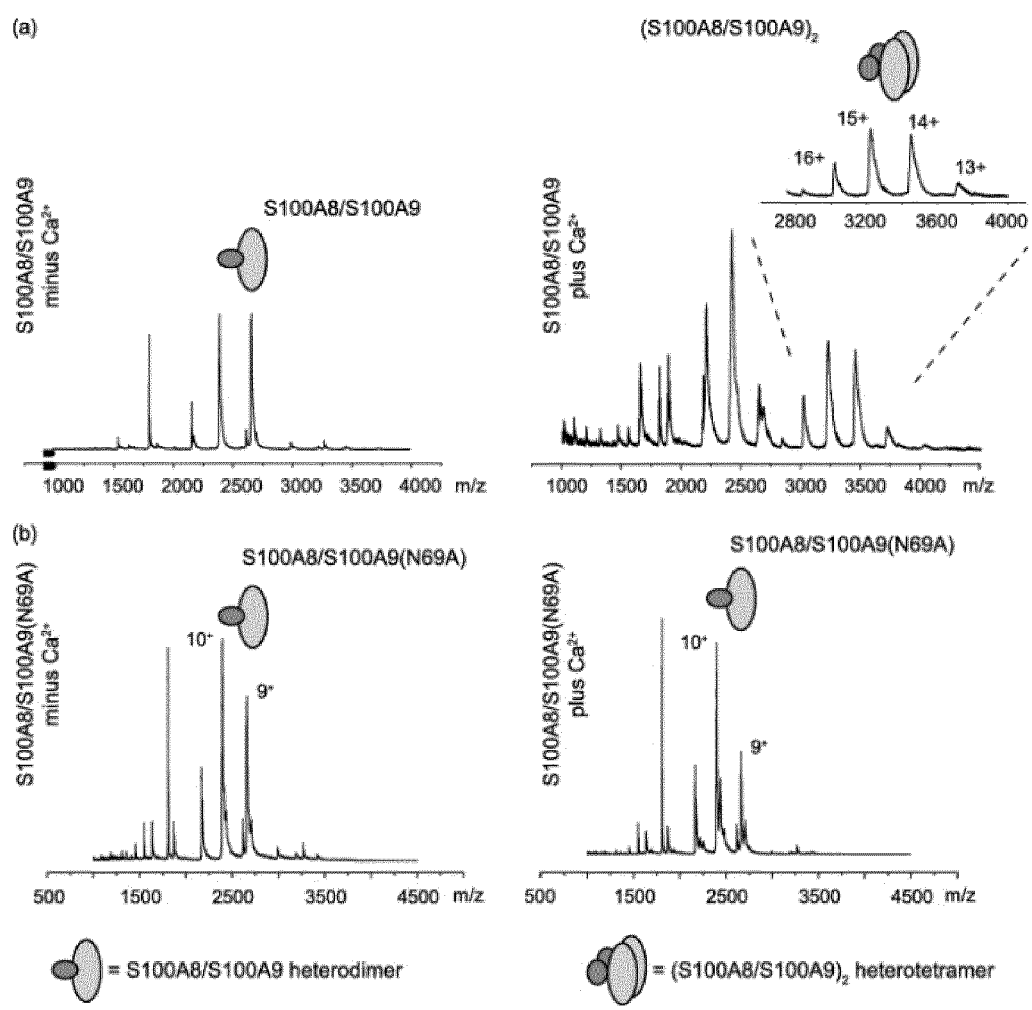
FIG. 6: ESI mass spectra in the absence and presence of calcium under native solvent conditions. (a) ESI mass spectra of recS100A8/S100A9 wild-type complexes. The mass spectra between m/z 1000 and 4000 together with an inset between m/z 2800 and 4000 are shown. In the absence of calcium (left) the main signals observed correspond to heterodimers with charge states 10+ and 9+. In the presence of calcium (right) signals corresponding to tetramers occurred at charge states 16+, 15+, 14+ and 13+ in the range between m/z 3000-3800. (b) ESI mass spectra of recS100A8/S100A9(N69A) mutant complexes. In the absence and presence of calcium the main signals correspond to heterodimers with charge states 10+ and 9+, no tetramers were found. recS100A8/S100A9(E78A) and recS100A8/S100A9(N69A+E78A) showed almost identical results (data not shown).

The oligomerization properties of the recS100A8/S100A9 mutant complexes can be determined by MALDI-MS. As shown exemplarily for the N69A mutant in FIG. 5(b), all mutant S100A9 proteins display signals for singly charged heterodimers in the absence of calcium. In contrast to the results obtained with the recS100A8/S100A9 wt proteins no heterotetramers can be observed for the mutant complexes in the presence of calcium (FIG. 5). The base peaks under these conditions exclusively represent S100A8/S100A9(N69A), S100A8/S100A9(E78A) and S100A8/S100A9(N69A+ E78A) heterodimers. All MALDI-MS experiments presented here were also confirmed by ESI-MS measurements (see FIG. 6).

Figure 7:
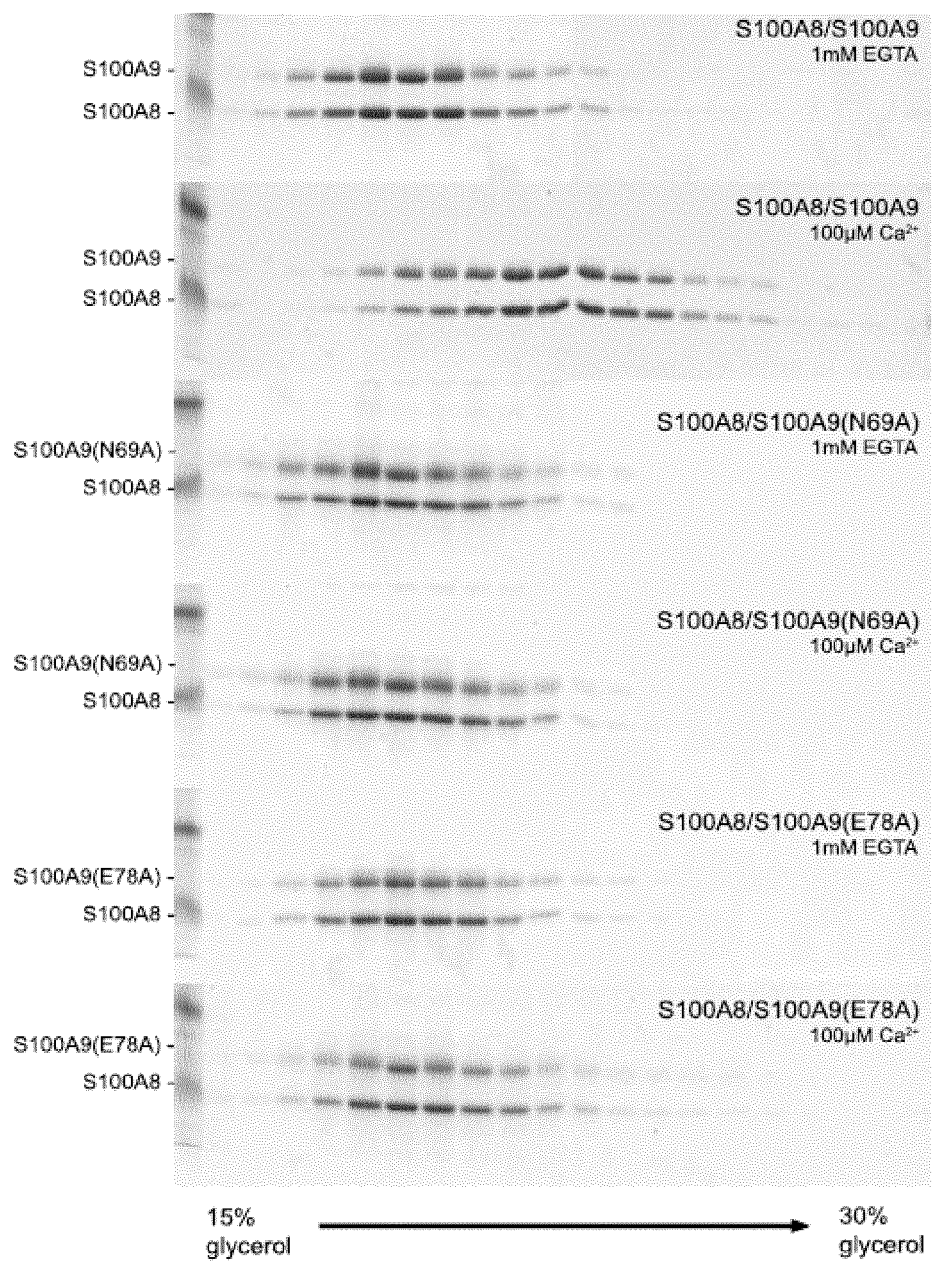
FIG. 7: Density gradient centrifugation of S100A8/ S100A9 proteins. wt and mutant recS100A8/S100A9 complexes were loaded on a glycerol gradient in the presence of either 1 mM EGTA or 100 µM Ca2+. After centrifugation, successive fractions of the gradients were analyzed by SDS-PAGE. In the presence of EGTA wt and mutant complexes showed an almost identical distribution centered in the low density fractions of the gradient. Addition of calcium induced a marked shift for recS100A8/S100A9 wt to higher glycerol densities, whereas for the mutant complexes recS100A8/S100A9(N69A) and recS100A8/S100A9 (E78A) no shift was observed.

Density gradient centrifugation can be employed in order to confirm the different complex formation patterns obtained in the mass spectrometric studies (FIG. 7). In EGTA-containing samples the recS100A8/S100A9 wt and mutant complexes are found in the same range of fractions of the glycerol gradient (19(±2)%), indicating that in the absence of calcium the formation of heterodimers is preferred in wt proteins and all S100A9 mutants. In the presence of calcium, wt complexes shifted to fractions of significantly higher glycerol concentrations (23(±2)%), as observed earlier for S100A8/S100A9 purified from granulocytes. This shift reflects the calcium-induced formation of high-molecular (S100A8/S100A9)$_2$ tetramers. In contrast, after addition of calcium, the mutant complexes recS100A8/S100A9(N69A) and recS100A8/S100A9(E78A) show no shift to higher glycerol concentrations, confirming that heterotetramer formation is disturbed.

Figure 8A:
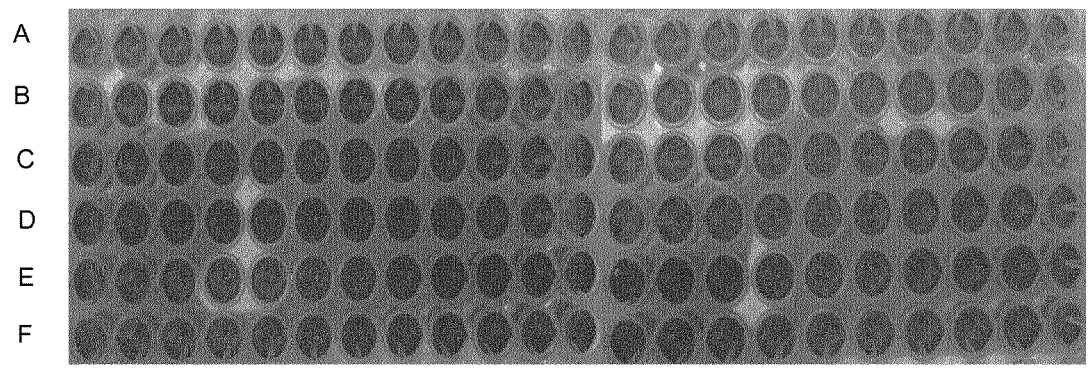
FIG. 8A: Protein concentrations of collected fractions determined by Bradford assay. Sample A: S100A12 wild type+2 mM EGTA, sample B S100A12 wild type+5 mM $CaCl_2$, sample C: S100A12 wild type+1 mM Zn, sample D S100A12 wild type+200 µM Zn, sample E: S100A12 wild type+5 mM $CaCl_2$+200 µM Zn, sample F: S100A12 wild type+2.5 mM $CaCl_2$+100 µM Zn
Figure 8B:
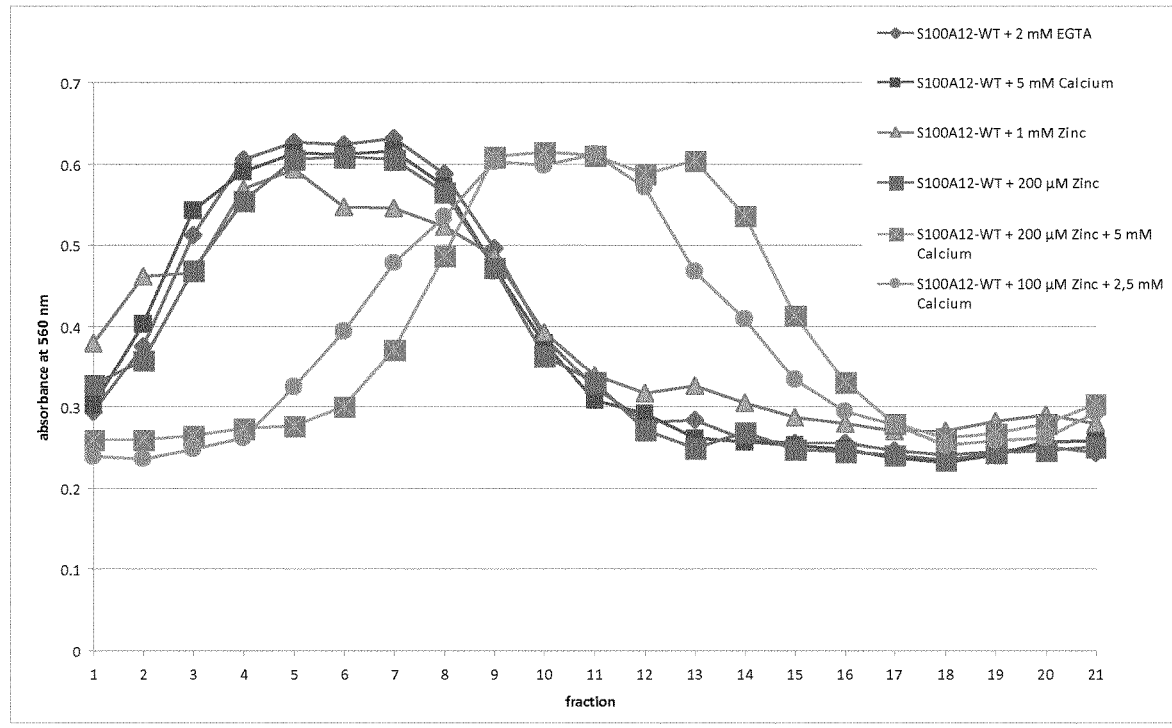
FIG. 8B: Summary of collected and analysed fractions of wtS100A12 (see FIG. 8A) in the presence or absence of bivalent cations as indicated in the figure.
Figure 8C:
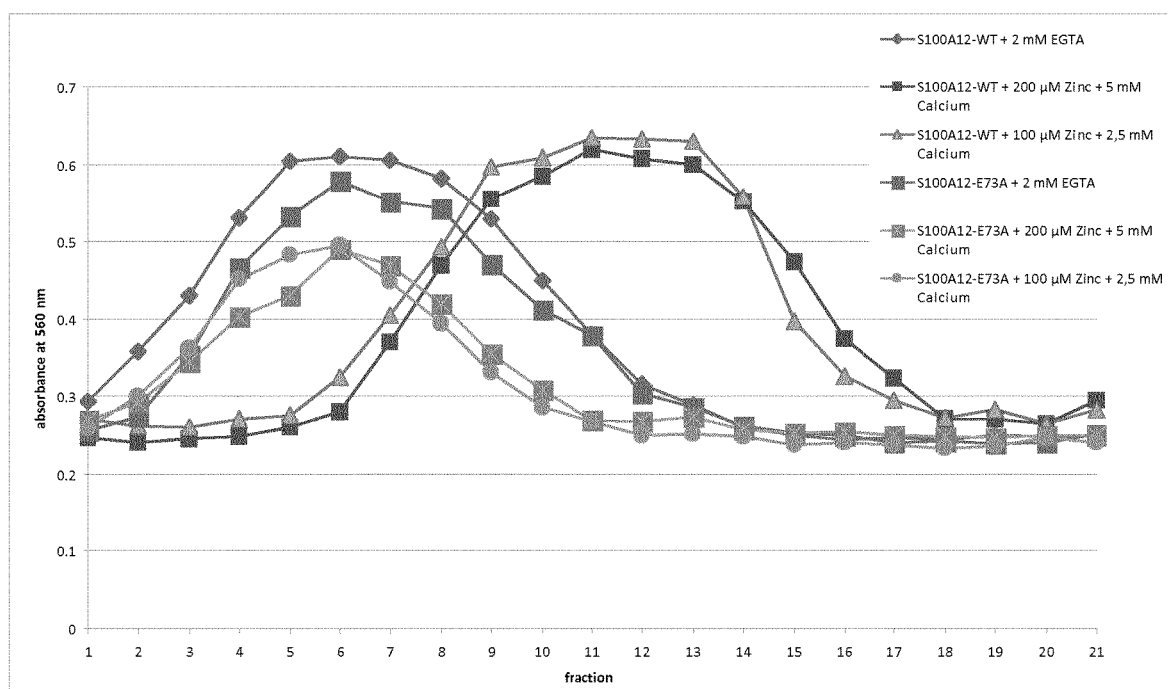
FIG. 8C Summary of collected and analysed fractions of wtS100A12 and recS100A12E73A mutant in the presence (5 mM $CaCl_2$+200 µM Zn, 2.5 mM $CaCl_2$+100 µM Zn) or absence (2 mM EGTA) of bivalent cations as indicated in the figure.

Example 2: Differences in Oligomerization States of S100A12 Wild Type and S100A12 Mutants Glycerol centrifugation can be employed in order to confirm the different complex formation patterns as previously observed for S100A8/S100A9 complexes. In EGTA-containing samples the recS100A12 wt and mutant rec S100A12E73A complexes are found in the same range of glycerol fractions 4-10 indicating that in the absence of calcium/zinc the formation of homodimers is preferred in wt proteins and the tested S100A12 mutant. In the presence of calcium or zinc alone wtS100A12 was found in the same fractions as observed before under EGTA-conditions, indicating that for S100A12 in contrast to S100A8/S100A9 calcium alone is not sufficient to induce oligomerization. However, in the presence of calcium and zinc, wild type S100A12 complexes shifted to fractions of significantly higher numbers (9-15). This shift reflects the calcium/zinc-induced formation of high-molecular S100A12 tetramers and hexamers. In contrast, after addition of calcium and zinc, the mutant complex recS100A12(E73A) shows no shift to higher glycerol fractions, confirming that tetramer/ hexamer formation is disturbed (FIG. 8).

The invention claimed is:

1. A S100A12 mutant, wherein the mutant comprises at least one mutation at an amino acid corresponding to amino acid His16, Ser19, Lys22, His24, Asp26, Thr27, Glu32, Asp62, Asn64, Asp66, Glu73, His86, or His90 of human S100A12 as set forth in SEQ ID NO: 01.

2. The mutant of claim 1, wherein the mutant is capable of forming S100A12 dimers.

3. The mutant of claim 1, wherein the mutant does not significantly form S100A12 tetramers or S100A12 hexamers.

4. The mutant of claim 1, wherein the mutant has a sequence identity of at least about 75%, 80%, 85%, 90%, 95%, 98%, 99%, or 100% as compared to any one of the sequences of SEQ ID NO: 05, SEQ ID NO: 06, or SEQ ID NO: 07 wherein the mutant is capable of forming S100A12 dimers and does not significantly form S100A12 tetramers or S100A12 hexamers.

5. A kit comprising a S100A12 mutant of claim 1.

6. A method of generating an antibody against the S100A12 mutant of claim 1, comprising administering to a mammal an antibody-generating peptide from human S100A12 as set forth in SEQ ID NO: 01, the peptide comprising one or more mutation(s) at an amino acid corresponding to amino acid His16, Ser19, Lys22, His24, Asp26, Thr27, Glu32, Asp62, Asn64, Asp66, Glu73, His86, or His90, and purifying the antibody.

7. The method of claim 6 wherein the one or more mutations is a glycine or alanine at said amino acid(s).

8. The method of claim 6 wherein the peptide comprises one, two, three, four, or five mutation(s) at an amino acid corresponding to amino acid Glu32, Asp62, Asn64, Asp66, or Glu73.

9. The mutant of claim 3, wherein the mutant has no more than 1% (w/w) impurity of the S100A12 tetramers or S100A12 hexamers.

10. The mutant of claim 4, wherein the mutant has no more than 1% (w/w) impurity of the S100A12 tetramers or S100A12 hexamers.

11. The mutant of claim 4, wherein the mutant has sequence identity of at least 95% as compared to any one of the sequences of SEQ ID NO: 05, SEQ ID NO: 06, or SEQ ID NO: 07.

12. The mutant of claim 11, wherein the mutant has sequence identity of at least 99% as compared to any one of the sequences of SEQ ID NO: 05, SEQ ID NO: 06, or SEQ ID NO: 07.

13. The mutant of claim 12, wherein the mutant has the following sequence: SEQ ID NO: 05, SEQ ID NO: 06, or SEQ ID NO: 07.

* * * * *